US010321856B2

United States Patent
Fu et al.

(10) Patent No.: US 10,321,856 B2
(45) Date of Patent: Jun. 18, 2019

(54) BED EXIT MONITORING SYSTEM

(71) Applicant: Hill-Rom Services, Inc., Batesville, IN (US)

(72) Inventors: Yongji Fu, Harrison, OH (US); Ibne Soreefan, West Chester, OH (US); Alexander Sheung Lai Wong, Waterloo (CA); Mohammad Javad Shafiee, Kitchener (CA); Brendan James Chwyl, Waterloo (CA); Audrey Gina Chung, Waterloo (CA)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 15/866,972

(22) Filed: Jan. 10, 2018

(65) Prior Publication Data
US 2018/0192923 A1  Jul. 12, 2018

Related U.S. Application Data

(60) Provisional application No. 62/445,312, filed on Jan. 12, 2017.

(51) Int. Cl.
*A61B 5/00* (2006.01)
*A61B 5/11* (2006.01)
*G08B 21/22* (2006.01)

(52) U.S. Cl.
CPC .......... *A61B 5/1128* (2013.01); *A61B 5/1115* (2013.01); *A61B 5/743* (2013.01); *G08B 21/22* (2013.01)

(58) Field of Classification Search
CPC .................................................. A61B 5/1128

USPC ........................................................ 340/573.4
See application file for complete search history.

(56) References Cited

U.S. PATENT DOCUMENTS

| | | | |
|---|---|---|---|
| 7,746,218 B2 | 6/2010 | Collins, Jr. et al. | |
| 9,489,820 B1* | 11/2016 | Kusens | A61B 5/746 |
| 10,074,184 B2* | 9/2018 | Rocque | G06T 7/13 |
| 2007/0136102 A1 | 6/2007 | Rodgers | |
| 2007/0157385 A1* | 7/2007 | Lemire | A61G 7/005 |
| | | | 5/600 |
| 2009/0044334 A1* | 2/2009 | Parsell | A61B 5/0064 |
| | | | 5/424 |
| 2012/0029879 A1* | 2/2012 | Sing | A61B 5/1116 |
| | | | 702/189 |

(Continued)

OTHER PUBLICATIONS

Extended European Search Report for Application No. 18150985.2 dated May 24, 2018.

(Continued)

*Primary Examiner* — Santiago Garcia
(74) *Attorney, Agent, or Firm* — Merchant & Gould P.C.

(57) ABSTRACT

A method for monitoring a patient in a bed may involve capturing images of the patient with multiple cameras in a vicinity of the bed, wirelessly transmitting the images of the patient from the multiple cameras to a processor including a memory device, processing the images to provide processed image data pertaining to a position of the patient relative to the bed to a user, and analyzing the processed image data to determine whether the patient is exiting the bed. The method may also optionally involve providing an alarm indicating that the patient is exiting the bed.

11 Claims, 5 Drawing Sheets

(56) References Cited

U.S. PATENT DOCUMENTS

| | | | |
|---|---|---|---|
| 2012/0075464 A1* | 3/2012 | Derenne | A61B 5/0013 |
| | | | 348/135 |
| 2013/0069780 A1 | 3/2013 | Tran et al. | |
| 2013/0246088 A1 | 9/2013 | Huster et al. | |
| 2014/0204207 A1 | 7/2014 | Clark et al. | |
| 2014/0253710 A1* | 9/2014 | Yasukawa | A61B 5/1128 |
| | | | 348/77 |
| 2014/0267625 A1* | 9/2014 | Clark | A61B 5/002 |
| | | | 348/46 |
| 2015/0048949 A1* | 2/2015 | Koblasz | G06F 19/3462 |
| | | | 340/573.4 |
| 2015/0109442 A1* | 4/2015 | Derenne | G16H 80/00 |
| | | | 348/143 |
| 2015/0112151 A1 | 4/2015 | Muhsin et al. | |
| 2015/0323388 A1* | 11/2015 | Kostic | A61G 13/10 |
| | | | 250/338.1 |
| 2016/0065909 A1 | 3/2016 | Derenne et al. | |
| 2016/0081594 A1 | 3/2016 | Gaddipati et al. | |
| 2016/0140827 A1 | 5/2016 | Derenne et al. | |
| 2016/0174909 A1 | 6/2016 | Collins, Jr. et al. | |
| 2016/0220114 A1* | 8/2016 | Norita | A61B 5/1117 |
| 2016/0302714 A1* | 10/2016 | Ng | G06K 9/00335 |
| 2017/0000356 A1* | 1/2017 | Smith, Sr. | A61B 5/02055 |
| 2017/0046577 A1* | 2/2017 | Rocque | A61B 5/6891 |
| 2017/0224253 A1* | 8/2017 | Berlin | A61B 5/1115 |
| 2018/0096576 A1* | 4/2018 | Anderholm | G08B 13/19695 |
| 2018/0144605 A1* | 5/2018 | Kusens | G08B 21/22 |
| 2018/0158192 A1* | 6/2018 | Rocque | A61B 5/1115 |

OTHER PUBLICATIONS

Yu, Xinguo, "Approaches and principles for fall detection for elderly and patient," 2008 10th IEEE Intl. Conf. on e-Health Networking, Applications and Service (Healthcom 2008), 6 pages.

Bustamante, P. et al., "In-Bed Patients Behaviour Monitoring System," https://scholar.google.com/scholar?hl=en&as_sdt=0,24&q=%22in-bed+patients+behaviour%22, © 2008 IEEE, 6 pages.

Wang, H. et al., "Dense trajectories and motion boundary descriptors for action recognition," International Journal of Computer Vision, Springer Verlag, 2013, 103 (1), 22 pages.

\* cited by examiner

BED EXIT MONITORING SYSTEM

RELATED APPLICATION(S)

This patent application claims the benefit of U.S. Patent Application Ser. No. 62/445,312 filed on Jan. 12, 2017, the entirety of which is hereby incorporated by reference.

BACKGROUND

The present application is related to a system and method for monitoring a patient to determine when the patient is exiting a bed. More specifically, the present application is directed to a bed exit monitoring system that uses one or more video cameras and a computer algorithm to process images for a viewer.

A patient in a care facility, such as a hospital, clinic, nursing home or the like, is often in a compromised medical condition and susceptible to developing complications. Injuries and complications sustained by patients in a care facilities result in significant healthcare costs. When these injuries or complications are considered preventable, the care facility acquired conditions may not be covered by a patient's insurer or other payers, such as Medicare. In an effort to prevent such injuries and complications, various protocols are implemented by the management of the care facilities to mitigate the risks. For example, the use of prophylactic antibiotics after surgery may be a standard institutional practice to mitigate the risk of surgical infections. As another example, patients who are at risk of falling when moving unassisted may be identified as fall risks, and certain protocols may be implemented to reduce the opportunity for the patient to move about the room unassisted.

In response to the desire of healthcare facilities to reduce risks, sensor systems to detect the status of various components of a patient support apparatus, such as a bed, have been developed, to help ensure that protocols are being met. For example, patient position monitoring systems monitor the movement of a patient on a bed and alarm if the movement is excessive or a patient has exited the bed. These systems may also include alarms for certain bed positions, such as the amount of elevation of the head section of the bed, to ensure that a patient is positioned with her upper body at an appropriate angle relative to gravity when various therapies are being delivered. The bed may also include sensors that detect when a side rail is in an appropriate position or that the brake system of the bed is properly engaged. This information may be provided to a central monitoring system, such as a nurse call system, so that deviations from the appropriate conditions may be monitored by the central system and alarms generated if a protocols are not being followed.

The use of these bed status variables requires that certain conditions be pre-established in the central monitoring system. For example, if the patient is a fall risk, the central monitoring system must be configured to monitor for side rail position and bed exit status for the particular patient support apparatus on which the fall risk patient is positioned. The same is true for other protocol monitoring conditions— the system must be configured for a particular patient, and the caregivers must modify the alarm conditions based on the particular protocols implemented for a given patient. Because of the required active intervention of the caregivers, protocols are often directed to particular classes of patients without regard to any patient or environmental based mitigating conditions. A change in status of a particular patient requires the caregiver to implement modified protocols and update any monitoring conditions that may need to be modified due to the change in the patient's condition.

Several conditions are of significant interest to caregivers based on the statistical incidence of care facility-based injuries or complications. For example, there is strong statistical support for a need to mitigate the risk of falls in patients who are 65 years or older. Other patient populations may also be at risk of falls, depending on other medical conditions that are normally assessed at the time of admission into a care facility. However, as with any statistic, there are exceptions that mitigate the risk, even in at-risk populations. As a result, applying a "one-size-fits-all" fall prevention program based on age may not provide a patient who has a low risk with the appropriate care for that particular patient. Patients who have mitigating conditions that significantly reduce the risk of fall, even though their age places them in a high-risk group, may be negatively impacted in their recovery if the highest fall prevention protocol is applied to them. Generally, a fall prevention program requires a patient to be assisted when ambulating. For a patient who feels healthy and is at low risk of falling, such a protocol may result in the patient being noncompliant to other protocols.

BRIEF SUMMARY

In one aspect of the present disclosure, a system for monitoring a patient in a bed may include multiple cameras in a vicinity of the bed, and a processor coupled wirelessly with the multiple cameras and including a memory device. The memory device includes instructions that, when executed by the processor, cause the processor to process video data captured by the multiple cameras and pertaining to a position of the patient relative to the bed and analyze the video data to determine whether the patient is exiting the bed. In some embodiments, the memory device further includes instructions that, when executed by the processor, cause the processor to determine a risk of the patient exiting the bed. The memory device may also include instructions that, when executed by the processor, cause the processor to pixilate the video data and highlight portions of an image of the patient to indicate that the patient is exiting the bed. Optionally, the memory device may further include instructions that, when executed by the processor, cause the processor to output a signal indicative of the patient exiting the bed. For example, the signal may be an alarm. In some embodiments, the memory device may also include instructions that, when executed by the processor, cause the processor to analyze a risk of a patient fall.

A method for monitoring a patient in a bed may involve: capturing images of the patient with multiple cameras in a vicinity of the bed; wirelessly transmitting the images of the patient from the multiple cameras to a processor including a memory device; processing the images to provide processed image data pertaining to a position of the patient relative to the bed to a user; and analyzing the processed image data to determine whether the patient is exiting the bed. In some embodiments, for example, the images are video images. Processing the images may involve pixilating the images and highlighting portions of the images of the patient to indicate that the patient is exiting the bed. In some embodiments, processing the images may involve dense sampling of the images in multiple spatial scales, tracking in each of the multiple spatial scales separately, and providing a trajectory description. In some embodiments, the analyzing step is performed by the user. The method may further involve providing an alarm indicating that the patient is exiting the bed.

These and other aspects and embodiments are described in greater detail below, in relation to the attached drawing figures.

DETAILED DESCRIPTION

Figure 1:
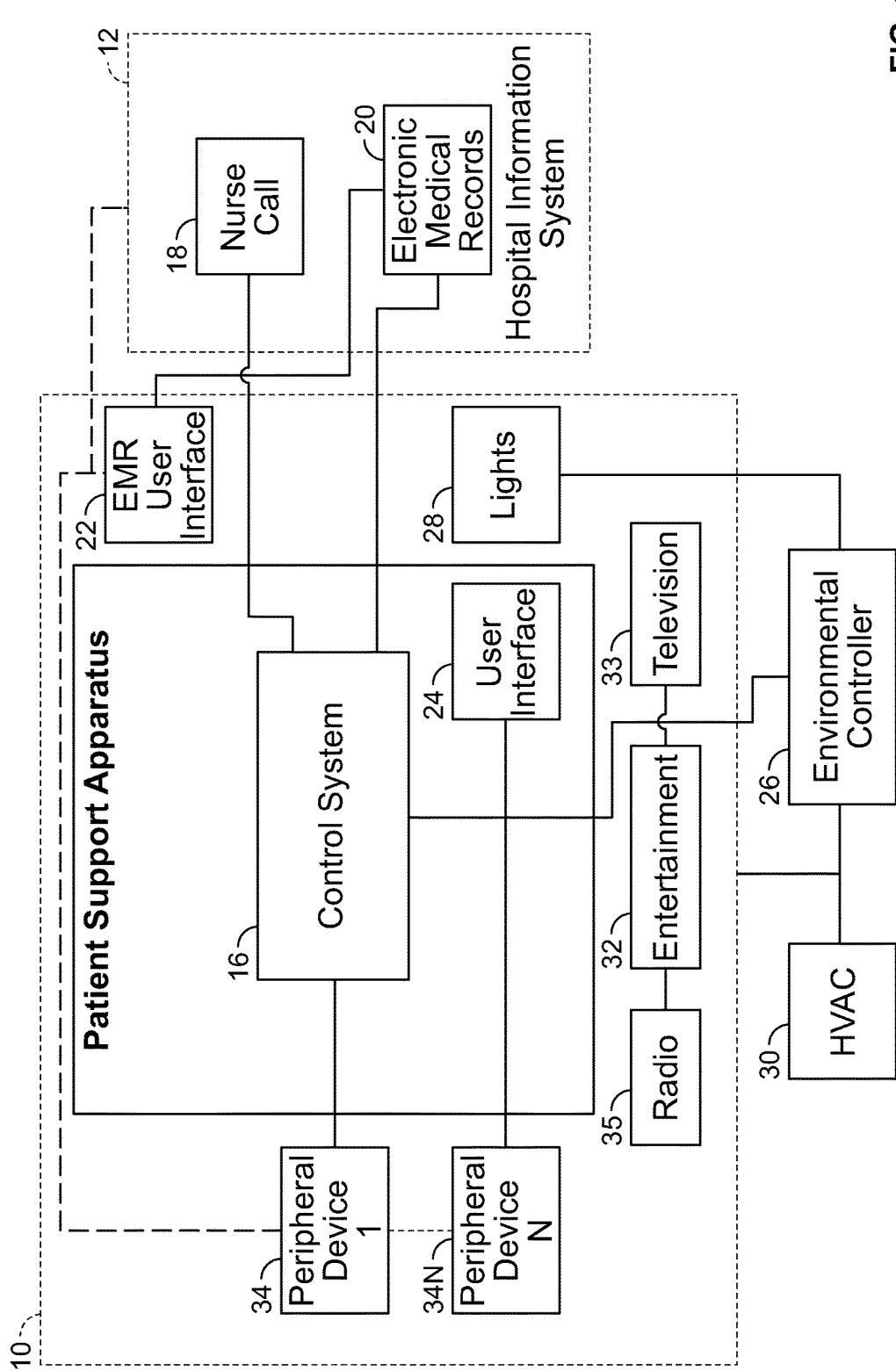
FIG. 1 is a diagrammatic view of a patient support apparatus positioned in a room, with a control system of the patient support apparatus in electrical communication with other devices, controllers, and systems positioned inside and outside the room.

The embodiments of the claimed subject matter and the various features and advantageous details thereof are explained more fully with reference to the non-limiting embodiments and examples that are described and/or illustrated in the accompanying drawings and detailed in the following description. The features illustrated in the drawings are not necessarily drawn to scale, and features of one embodiment may be employed with other embodiments, even if not explicitly stated herein. Descriptions of well-known components and processing techniques may be briefly mentioned or omitted, so as to not unnecessarily obscure the embodiments of the claimed subject matter described. The examples used herein are intended merely to facilitate an understanding of ways in which the claimed subject matter may be practiced and to further enable those of skill in the art to practice the embodiments of the claimed subject matter described herein. Accordingly, the examples and embodiments herein are merely illustrative and should not be construed as limiting the scope of the claimed subject matter, which is defined solely by the appended claims and applicable law. Moreover, like reference numerals may represent similar parts throughout the several views of the drawings.

The present disclosure describes improved methods and systems for monitoring patients in care facility rooms, for example to monitor whether patients are exiting their beds. The methods and systems may assist caregivers in preventing unadvised, unmonitored bed exits and thus help prevent patient falls. The methods and systems may also allow for different patients to be monitored with varying levels of scrutiny, based at least in part on the needs of the individual patients, and may facilitate efficient and effective monitoring of multiple patients by an observer.

FIG. 1 is a diagrammatic representation of the relationship between a patient support apparatus 14 positioned in a room 10 of a care facility and a hospital information system 12, according to one embodiment. This figure and details of other aspects and embodiments are described in U.S. Patent Application Pub. No. 2013/0246088, titled "Algorithm for Predicting and Mitigating Adverse Events," the full disclosure of which is hereby incorporated by reference. This exemplary embodiment is provided here as one example of an environment in with a patient support apparatus 14 may be positioned and used. It is not intended to be limiting but only exemplary.

In the illustrated embodiment, the hospital information system 12 includes a centralized nurse call system 18 and a centralized electronic medical record system 20. Both the nurse call system 18 and electronic medical records system 20 include information that is related to a patient support apparatus 14 and associated with the patient stored in memory as related records. The information related to the patient stored in memory in the nurse call system 18 and electronic medical records system 20 is constantly updated as information is added to the electronic medical records system 20 and the nurse call system 18 receives information related to the patient and the patient support apparatus 14.

The patient support apparatus 14 includes a control system 16 that is in communication with the nurse call system 18. The control system 16 includes a user interface 24 that is used by the patient supported on the patient support apparatus 14 or a caregiver to provide inputs to the control system 16 or display outputs from the control system 16. As shown diagrammatically in FIG. 1, the electronic medical records system 20 is in electrical communication with a user interface 22 positioned in the room 10 and accessible by caregiver to input patient information and enter orders while the caregiver is in the room 10. The user interface 22 may be a personal computer or a dedicated peripheral device. It should be understood that other user interfaces may be used throughout a facility to interface with the hospital information system 12, and specifically the electronic medical records system 20. In the illustrative embodiment of FIG. 1, the user interface 24 is positioned on the patient support apparatus 14 and may be used by caregiver to access the electronic medical records system 20 through the control system 16 of the patient support apparatus 14, which is in direct communication with the electronic medical records system 20 and acts as a peripheral device to the electronic medical records system 20.

The control system 16 is also in communication with an environmental systems controller 26, which provides an interface between the patient support apparatus 14 and various environmental systems including lights 28, heating-ventilating-air-conditioning system 30, and entertainment devices 32 such as a television 33 or radio 35, for example. The environmental systems controller 26 provides information to the control system 16 and acts on instructions from the control system 16 to modify operation of the environmental systems. Some of the information provided by the environmental systems controller 26 is stored in memory associated with the environmental systems controller 26. The information provided by the environmental systems controller 26 is updated as operating parameters of the environmental systems change.

The control system 16 may also be in communication with one or more peripheral devices 34 positioned in the room 10. The peripheral devices 34 each perform a therapy or diagnostic function. For example, the peripheral device 34 may be a ventilator, heart monitor, blood pressure monitor, infusion device, blood oxygen monitor, sequential compression device, high-frequency chest wall oscillation device, or another standalone diagnostic or therapeutic device. Information used by the control system 16 may be stored in memory associated with a peripheral device 34, including the therapy parameters or current operating conditions of the peripheral device 34. In addition, diagnostic values such as a heart rate, blood pressure, or other diagnostic values may be stored in memory associated with the peripheral device. In some cases, the peripheral devices 34 may communicate to the controller 26 via a network connection such as a controller area network (CAN) and information stored on a controller of the device 34 may be accessible by the controller 26. In other cases, the information may be stored by the hospital information system 12. In still other cases, the peripheral devices 34 may communicate with the controller 26 and the controller 26 may store information related to the operator of the peripheral device(s) 34 in memory of the controller 26. As illustrated in FIG. 1, any number of peripheral devices 34 may be in communication with the patient support apparatus 14. It should be understood that peripheral devices such as the peripheral devices 34, may be in direct communication with the hospital information system 12 without being connected through the patient support apparatus 14.

The nurse call system 18 generates alarms and notifies caregivers of alarm conditions based on signals from the control system 16 of the patient support apparatus 14. It is also known in the art for the patient support apparatus 14 to provide a communication link such as audio or video communications between a patient supported on the patient support apparatus 14 and a nurse positioned at a central nurse call station 18. It is also known for caregivers to carry communication badges that include telephone or other voice communication capability, with the badges providing a direct communication between the caregiver and the central nurse call station 18 or patient, such as the system disclosed in U.S. Pat. No. 7,746,218 titled "Configurable System for Alerting Caregivers," incorporated by reference herein. The nurse call system and/or communication badges may facilitate direct communication between a caregiver and a patient positioned on any patient support apparatus is 14 throughout a care facility. In this way, the nurse call system 18 acts as a dispatch system to provide instructions to caregivers when various conditions warrant the intervention of the caregiver either to make adjustments to equipment or to respond to the needs of a particular patient.

As mentioned above, various embodiments described herein provide a method and system for monitoring a patient in a hospital bed or other patient support apparatus to determine if or when the patient is exiting the bed. For clarity, the patient support apparatus referenced above will be referred to below as a "bed." In alternative embodiments, however, the patient support apparatus may be a chair, a recliner, or any other patient support apparatus. The bed may be located in the patient's home or in any patient care facility, such as but not limited to a hospital, clinic, surgicenter, nursing home, skilled nursing facility, or the like.

Generally, the patient bed exiting method involves capturing a video image feed (with one or more video cameras) of a patient in a bed, sending the video feed through a network to a processor, analyzing the video feed with the processor to detect and evaluate patient movement, and providing a processed version of the video feed to a user/observer who is monitoring the patient. For example, the processor may use a computer algorithm to pixilate the video image feed, make determinations about how the patient is moving, relative to the bed, and determine whether the patient is moving in a way that indicates he/she is exiting the bed. If the algorithm determines that the patient is likely exiting the bed, the algorithm may highlight portions of the video image, such as the patient's body or a portion of the patient's body, to indicate that the patient is exiting the bed. Thus, the processed video feed may be easier for the observer to monitor, because anytime a patient moves in a way that is indicative of exiting the bed, the patient and/or other portion(s) of the video feed are highlighted to alert the observer. This may help make patient monitoring easier and more effective, while requiring less training of the observer. Additionally, in many scenarios a patient observer may be responsible for monitoring multiple patients simultaneously, for example on multiple video display monitors or on a split screen on one monitor. The method and system described herein may facilitate such observation of multiple patients simultaneously.

Figure 2:
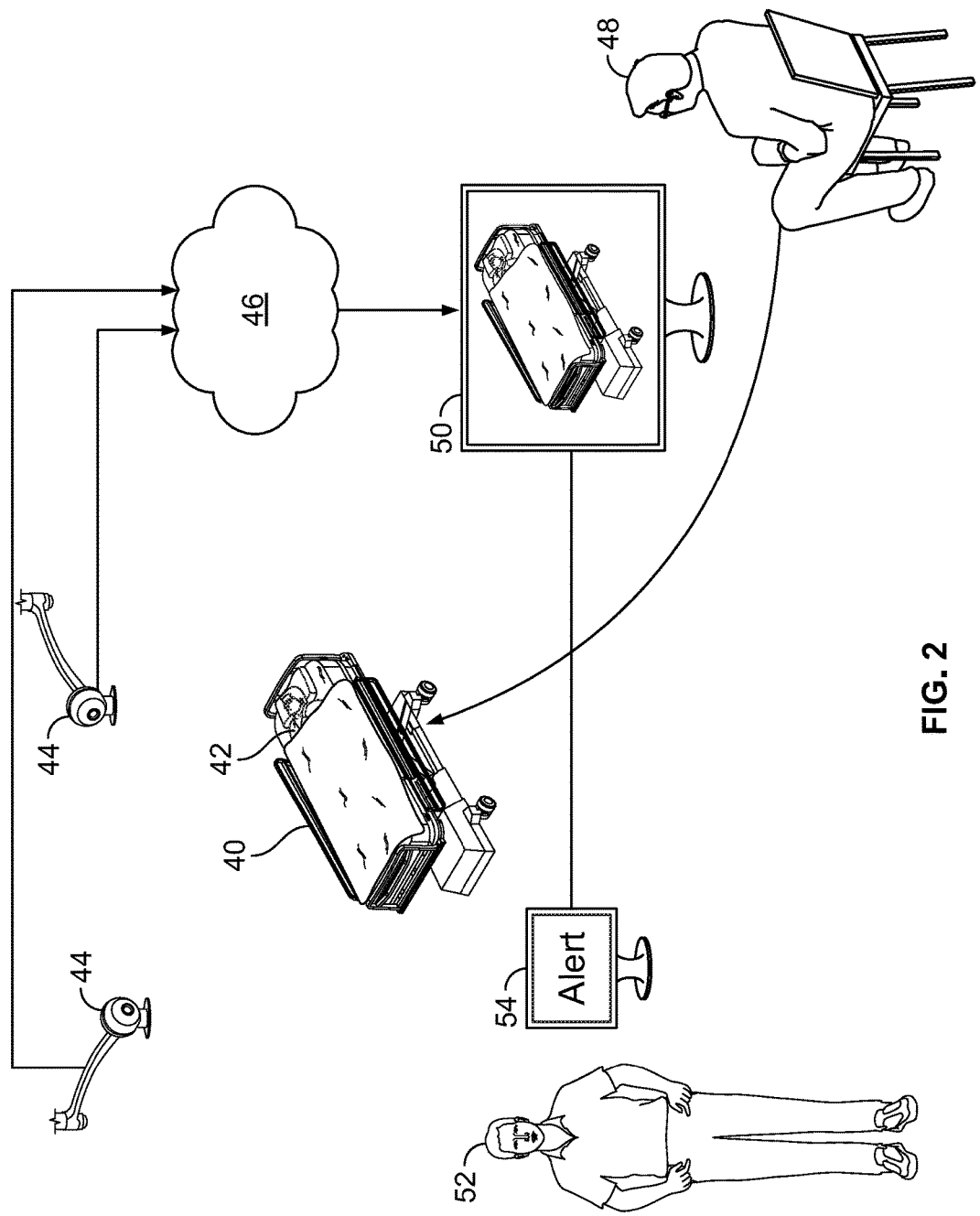
FIG. 2 is a diagrammatic view of a flow of patient image information from a patient's room to a user and a caregiver, according to one embodiment.

FIG. 2 is a simplified, diagrammatic representation of a method as just described, according to one embodiment. The figure illustrates an exemplary data flow from a patient's room to a caregiver and/or back to the patient's room. In the illustrated embodiment, a patient 42 lies on a bed 40. Multiple video cameras 44 in the vicinity of the bed 40 collect video images of the patient and transmit image signal data wirelessly through a network 46 to a computing device 50, including, for example, a processor, tangible memory, and a display. In various alternative embodiments, any suitable number of video cameras 44 may be used. Although two cameras 44 are illustrated in FIG. 2, in many embodiments one camera 44 may be sufficient, and in other embodiments more than two cameras 44 may be used. The network 46 may include the cloud, be positioned locally in the patient's room, elsewhere in the patient care facility, or any other suitable location.

As mentioned above, the computing device 50 uses an algorithm to process the video image data, such as local video processing and/or other channels, such as load cell and red sock technologies. The computing device 50 processes the image signal data and then provides processed image data to a user 48 (or "observer" or "monitor"), typically in the form of video images feeds of the patient 42 on a video display of the computing device 50. The user 48, in some embodiments, may be a trained observer. In one embodiment, the processed image data is a video feed that is highlighted in one color or a combination of colors, if and when the patient 42 is exiting the bed 40. The determination of when and how to highlight the image data is made by an algorithm housed in the memory of the computing device 50. The user 48 may be viewing multiple displays at one time, with each display providing video images for a different patient. Highlighting or otherwise marking images of patients 42 who are exiting their beds may make it easier and more effective for the user 48 to monitor multiple patients 42 simultaneously.

When the user 48 sees the patient 42 exiting the bed 40, she may alert a caregiver 52 that the patient 42 is exiting. This alert may be delivered in any suitable form, such as a text message, pager message, email, or other form of alert information, such as a message on a second display device 54 that is near to the care provider 52, such as at a nurses station in a hospital or skilled nursing facility. Alternatively or additionally, the user 48 may also provide an alert or reminder to the patient 42 to stay in bed, to be careful when exiting the bed, or the like. The alert or reminder may be provided, for example, via a voice command delivered over a microphone/intercom system in the patient's room.

In various embodiments, the user 48 may provide the reminder using voice or by entering information on a computer that results in delivery of a recorded message in the patient's room. Finally, the user 48 may tag the video image information with a note of some kind, indicating the observation of the patient 42 leaving the bed 40. This tag may be used later, by the system, to further develop the algorithm. In some alternative embodiments, the computing device 50 may do all image processing and providing of alerts, so that the user 48 is not necessary. However, in many embodiments it may be advantageous to include the user 48 in the process, for example to customize care for different patient needs.

Figures 3A, 3B, 3C:
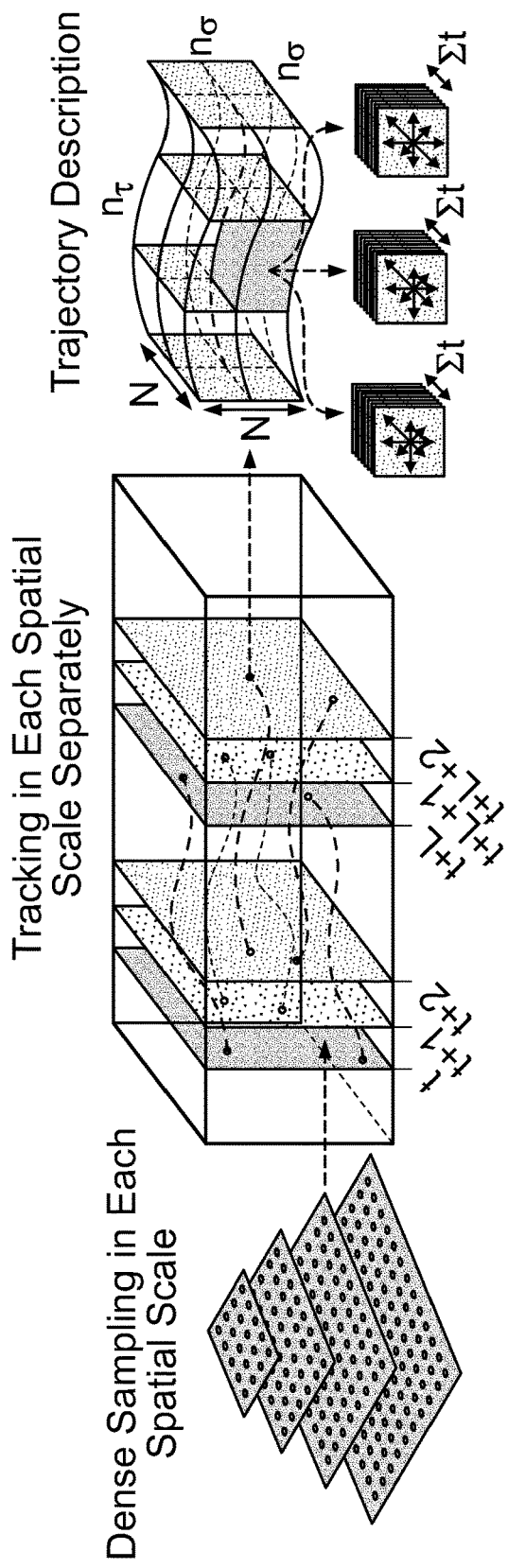
FIGS. 3A-3C illustrate the flow of image data through an image processing algorithm, according to one embodiment.

FIGS. 3A-3C are diagrammatic representations of one aspect of an image processing algorithm that may be used in the method and system described herein, according to one embodiment. Specifically, FIGS. 3A-3C illustrate an approach to extract and characterize dense trajectories and compute trajectory-aligned descriptors, as described in the article "Dense trajectories and motion boundary descriptors for action recognition," by Wang, H., et al., *International Journal of Computer Vision*, Springer Verlag, 2013, 103 (1), pp. 60-79, which is hereby incorporated fully herein by reference. FIG. 3A illustrates that the algorithm may first involve densely sampling feature points on a grid for each spatial scale. FIG. 3B illustrates that the algorithm may then carry out tracking in the corresponding spatial scale for L frames by median filtering in a dense optical flow field. FIG. 3C illustrates that the algorithm may then represent the trajectory shape by relative point coordinates and compute the descriptors (HOG, HOF, MBH) along the trajectory in a N×N pixels neighborhood, which is divided into nσ×nσ×nτ cells. (MBH stands for motion boundary histograms, HOG stands for histograms of oriented gradients, and HOF stands for histograms of optical flow.)

Referring to FIG. 3A, the algorithm may first densely sample feature points on a grid spaced by W pixels. Sampling may be carried out on each spatial scale separately. This helps ensure that feature points equally cover all spatial positions and scales. In one embodiment, a sampling step size of W=5 pixels may be used. In some embodiments, the algorithm may track all these sampled points through the video. However, in homogeneous image areas without any structure, it is impossible to track any point, so points in these areas are removed.

Referring to FIG. 3B, feature points may be tracked on each spatial scale separately. For each frame It, its dense optical flow field ωt=(ut, vt) is computed with regard to the next frame It+1, where ut and vt are the horizontal and vertical components of the optical flow. Once the dense optical flow field is computed, points can be tracked very densely without additional cost. Another advantage of the dense optical flow is the smoothness constraints, which allow relatively robust tracking of fast and irregular motion patterns.

Referring to FIG. 3C, the algorithm may next compute descriptors within a space-time volume aligned with a trajectory, to encode the motion information. The size of the volume is N×N pixels and L frames long. To embed structure information, the volume is subdivided into a spatio-temporal grid, a descriptor (HOG, HOF or MBH) is computed in each cell of the spatio-temporal grid, and the final descriptor is a concatenation of these descriptors. Additional details of this image processing method may be found in the above-referenced article.

In some embodiments, the end result of the video image processing is that patients moving in certain ways are highlighted in the video feed provided to the user/observer. The algorithm may identify, for example, patients who are moving toward the edges of their beds, as if to exit the bed by falling or standing up out of the bed. Using the above-described image processing technique, as one example, pixels of the video feed for patients moving toward or into a bed exit may be highlighted, for example by making them a certain color. This highlighting of pixels may help the observer quickly and easily see patients who are moving toward a bed exit, and the observer can then alert the patient and/or a caregiver.

Figure 4A:
FIGS. 4A-4F are highlighted patient images, showing a patient exiting a bed, according to one embodiment.
Figure 4B:
Figure 4C:
Figure 4D:
Figure 4E:
Figure 4F:

FIGS. 4A-4F are still images taken from a video image feed of a patient exiting his bed. In FIG. 4A, the patient is still mostly reclined in his bed, and in FIG. 4F he is standing and out of his bed. As indicated by the highlighting of various pixels making up the images of the patient, the algorithm processed the incoming video feed, determined that the patient was moving in a way that was indicative of a possible bed exit, and highlighted the patient in the processed video feed.

As mentioned above, and referring now to FIG. 5, in some embodiments, an observer may be viewing video feeds of multiple patients in multiple beds (often located in multiple different rooms) simultaneously. This may be accomplished, for example, by displaying the video feeds on multiple monitors or on one monitor with a split screen. In such a scenario, it may be difficult for the observer to carefully and effectively monitor all the patients to detect bed exits by one or more of the patients. Even when bed exits are detected by such an observer, they may sometimes be detected too late, due to the difficulty of monitoring multiple patients at once. This multi-patient observation may be especially challenging over a long period of time, such as a hospital shift or other time period in which the observer works. The method and system described herein may facilitate such a multi-patient monitoring process, by providing video feeds in which patients who are exiting their beds or moving as if to exit their beds are highlighted in some way, while patients who are not exiting their beds are not highlighted. Thus, an observer who is watching multiple feeds of multiple patients would have his/her eyes drawn more quickly toward the display monitors or subsections of monitors with highlighted feeds.

Figure 5:
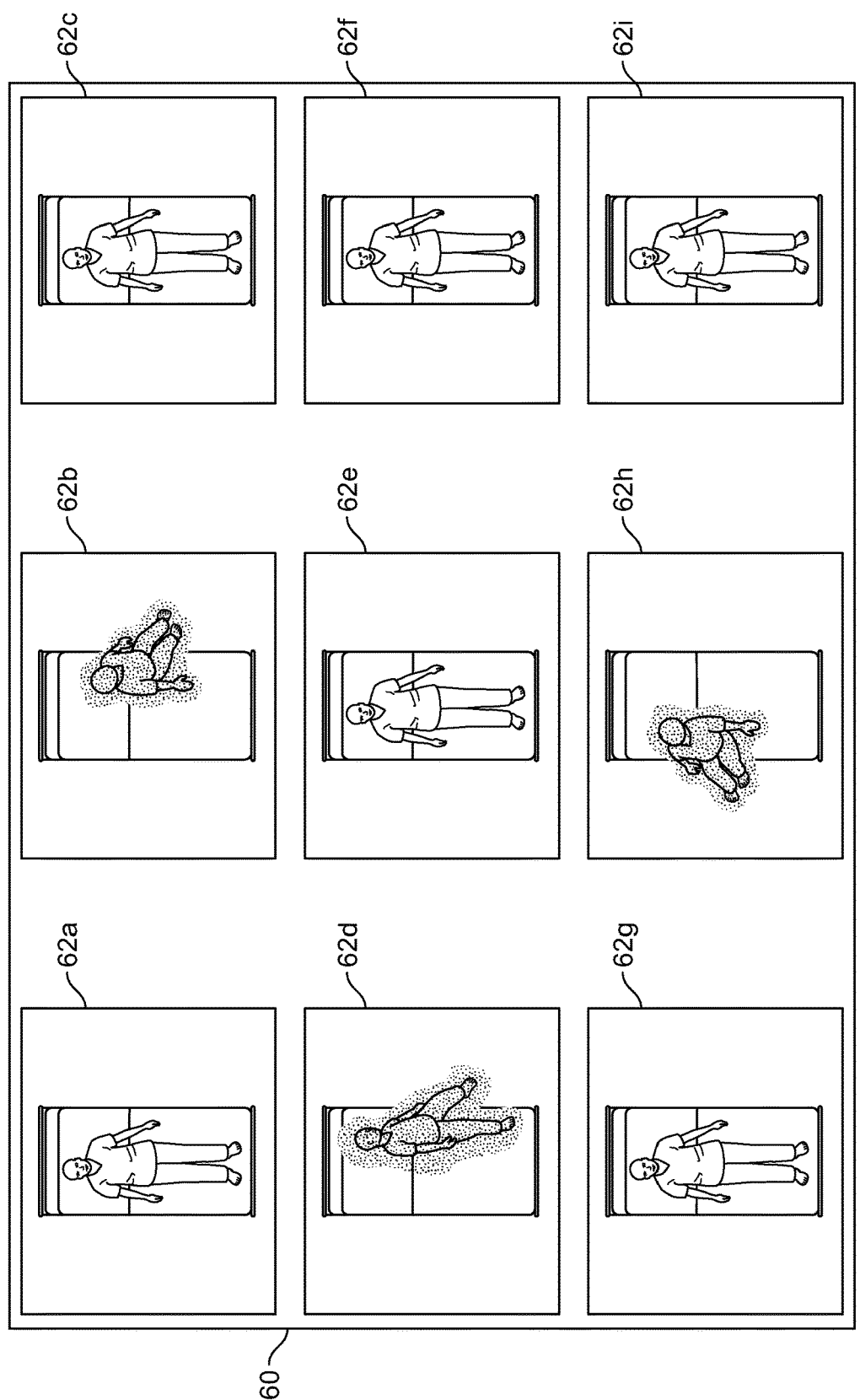
FIG. 5 is a diagrammatic representation of a display screen 60 divided into multiple smaller displays.

FIG. 5 is a diagrammatic representation of a display screen 60 or graphic user interface (GUI) divided into multiple smaller displays 62a-62i, each of which represents a video feed from a room of a different patient. As illustrated figuratively here, the patients in displays 62a, 62c, 62e, 62f, 62g and 62i are in their beds and have not been identified by the image processing algorithm as moving an a way indicative of a possible bed exit. The patients in displays 62b, 62d and 62h, however, have been identified by the algorithm as moving in a way indicative of a bed exit, and the patients have thus been highlighted in the video feed. Again, in some embodiments, the highlighting of a patient may be provided by coloring various pixels of the video feed of the patient. Alternatively, any other method may be used by the algorithm to highlight video images of a moving patient. For example, the image of the patient may be magnified or moved to the forefront of the video image, the background of the video feed may be given a different color than the background of non-active patients, an alert may be provided on the screen, the background may flash or strobe, the entire image may expand, or the like. In some embodiments, the processed video feed may employ multiple different techniques for drawing the observer's eye to the feeds of bed exiting patients. In short, any suitable method (or methods) of drawing an observer's attention toward a certain video feed may be used.

As a final step (or steps), the method may include the observer/user providing a message of some sort to the patient, a caregiver or both. For example, the observer might have a microphone connected to the patient's room, so that he/she can tell the patient to return to bed or provide other advice using vocal commands. In other embodiments, the observer might be able to adjust the patient's bed remotely, for example to raise one or both arms of the bed to prevent the patient from rolling out of the bed. Additionally or alternatively, the observer may also provide a message of some kind to a caregiver, such as a nurse, physician, other healthcare worker, nursing home worker, family member or the like. Such a message may include, for example, a text message, a page, a voice message over an intercom system, an email message, a phone call, or any other suitable message.

Using the above described system and method, a patient observer or monitor should be able to watch multiple patients in multiple beds more effectively than with previously available systems and methods. Therefore, the system and method may help prevent patient falls from bed and unwanted patient bed exits in general, thus reducing healthcare costs and enhancing patient care. The system and method may also conserve healthcare spending by requiring fewer patient observers and possibly by requiring less training of such observers.

The use of the terms "a" and "an" and "the" and similar referents in the context of describing the subject matter (particularly in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Furthermore, the foregoing description is for the purpose of illustration only, and not for the purpose of limitation, as the scope of protection sought is defined by the claims as set forth hereinafter together with any equivalents thereof entitled to. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

We claim:

1. A system for monitoring a patient in a bed, the system comprising:
   multiple cameras in a vicinity of the bed;
   a processor coupled wirelessly with the multiple cameras and including a memory device, the memory device including instructions that, when executed by the processor, cause the processor to:
   process video data captured by the multiple cameras and pertaining to a position of the patient relative to the bed and analyze the video data to determine whether the patient is exiting the bed; and
   pixilate the video data and highlight portions of an image of the patient to indicate that the patient is exiting the bed.

2. The system of claim 1, wherein the memory device further includes instructions that, when executed by the processor, cause the processor to determine a risk of the patient exiting the bed.

3. The system of claim 1, wherein the memory device further includes instructions that, when executed by the processor, cause the processor to output a signal indicative of the patient exiting the bed.

4. The system of claim 3, wherein the signal comprises an alarm.

5. The system of claim 1, wherein the memory device further includes instructions that, when executed by the processor, cause the processor to analyze a risk of a patient fall.

6. A method for monitoring a patient in a bed, the method comprising:
   capturing images of the patient with multiple cameras in a vicinity of the bed;
   transmitting the images of the patient from the multiple cameras to a processor including a memory device;
   processing the images to provide processed image data pertaining to a position of the patient relative to the bed, the processing including:
   pixilating the images, and
   highlighting portions of the images of the patient to indicate that the patient is exiting the bed; and
   analyzing the processed image data to determine whether the patient is exiting the bed.

7. The method of claim 6, wherein the images comprise video images.

8. The method of claim 6, wherein processing the images comprises:
   dense sampling of the images in multiple spatial scales;
   tracking in each of the multiple spatial scales separately; and
   providing a trajectory description.

9. The method of claim 6, wherein the analyzing step is performed by a user.

10. The method of claim 6, further comprising providing an alarm indicating that the patient is exiting the bed.

11. The method of claim 6, further comprising wirelessly transmitting the images of the patient from the multiple cameras to the processor.

* * * * *